United States Patent
Weisbart

(10) Patent No.: US 9,421,394 B2
(45) Date of Patent: Aug. 23, 2016

(54) QUANTUM FIELD SYSTEM FOR TREATMENT OF HUMAN TISSUE

(71) Applicant: Paul Weisbart, Haiku, HI (US)

(72) Inventor: Paul Weisbart, Haiku, HI (US)

(73) Assignee: Soliton Lasers, Haiku, HI (US)

( * ) Notice: Subject to any disclaimer, the term of this patent is extended or adjusted under 35 U.S.C. 154(b) by 0 days.

(21) Appl. No.: 14/081,030

(22) Filed: Nov. 15, 2013

(65) Prior Publication Data
US 2014/0142645 A1   May 22, 2014

Related U.S. Application Data

(60) Provisional application No. 61/727,224, filed on Nov. 16, 2012.

(51) Int. Cl.
| | | |
|---|---|---|
| A61N 1/00 | (2006.01) | |
| A61N 5/00 | (2006.01) | |
| A61N 2/00 | (2006.01) | |
| A61N 1/40 | (2006.01) | |
| A61N 5/06 | (2006.01) | |

(52) U.S. Cl.
CPC .. *A61N 5/00* (2013.01); *A61N 2/00* (2013.01); *A61N 1/40* (2013.01); *A61N 5/0618* (2013.01)

(58) Field of Classification Search
USPC ....................................................... 607/2, 89
See application file for complete search history.

(56) References Cited

U.S. PATENT DOCUMENTS

| | | |
|---|---|---|
| 4,649,935 A | 3/1987 | Charmillot et al. |
| 4,765,322 A | 8/1988 | Charmillot et al. |
| 4,930,504 A | 6/1990 | Diamantopoulos et al. |
| 4,951,663 A | 8/1990 | L'Esperance, Jr. |
| 5,358,503 A | 10/1994 | Bertwell et al. |
| 5,464,436 A | 11/1995 | Smith |
| 5,549,660 A | 8/1996 | Mendes et al. |
| 5,616,140 A | 4/1997 | Prescott |
| 5,755,752 A | 5/1998 | Segal |
| 5,800,479 A | 9/1998 | Thiberg |
| 5,830,211 A | 11/1998 | Santana et al. |
| 6,019,482 A | 2/2000 | Everett |
| 6,187,029 B1 | 2/2001 | Shapiro et al. |
| 6,443,978 B1 | 9/2002 | Zharov |
| 6,454,791 B1 | 9/2002 | Prescott |
| 6,602,275 B1 | 8/2003 | Sullivan |
| 6,702,837 B2 | 3/2004 | Gutwein |
| 6,872,221 B2 | 3/2005 | Lytle |

(Continued)

FOREIGN PATENT DOCUMENTS

WO    2010007614    1/2010

OTHER PUBLICATIONS

International Search Report in corresponding PCT application No. (PCT/US2013/070312) mailed Feb. 4, 2014.

(Continued)

*Primary Examiner* — Nicole F Lavert
(74) *Attorney, Agent, or Firm* — Banner & Witcoff, Ltd.

(57) ABSTRACT

There is disclosed a quantum field energy generating system that emits quantum energy to the body to provide a therapeutic and quantum effect to treat human tissue for health, rejuvenation and wellness. The quantum field generating system may include a housing, a printed circuit board contained within the housing, and a plurality of antennas positioned in the housing which may provide phased signals that provide a quantum field of energy for the treatment of human tissue.

17 Claims, 2 Drawing Sheets

(56) References Cited

U.S. PATENT DOCUMENTS

| | | |
|---|---|---|
| 8,236,037 B2 | 8/2012 | Weisbart et al. |
| 8,333,756 B2 | 12/2012 | Weisbart et al. |
| 2002/0198575 A1 | 12/2002 | Sullivan |
| 2004/0030370 A1 | 2/2004 | Lytle |
| 2008/0183161 A1 | 7/2008 | Walneck et al. |
| 2009/0112296 A1 | 4/2009 | Weisbart et al. |
| 2009/0227996 A1 | 9/2009 | Powell et al. |
| 2011/0021863 A1 | 1/2011 | Burnett et al. |
| 2011/0087306 A1* | 4/2011 | Goossen ............... A61N 1/3718 607/60 |
| 2011/0172747 A1* | 7/2011 | Weisbart et al. ................ 607/89 |
| 2013/0110207 A1 | 5/2013 | Weisbart et al. |

OTHER PUBLICATIONS

International Search Report in corresponding PCT application No. (PCT/US2011/023597) mailed Oct. 24, 2011.

Canadian Office Action in related Canadian application No. 2,772,404; dated Aug. 21, 2012.

Final U.S. Office Action in related U.S. Appl. No. 12/258,082; dated Apr. 13, 2012.

* cited by examiner

QUANTUM FIELD SYSTEM FOR TREATMENT OF HUMAN TISSUE

CROSS REFERENCE TO RELATED APPLICATIONS

This Application is a non-provisional application of U.S. application Ser. No. 61/727,224, filed on Nov. 16, 2012, which is incorporated by reference in its entirety.

FIELD OF THE INVENTION

The present invention relates generally to a system that provides a quantum field of energy that surrounds the body to provide a therapeutic and quantum healing effect to treat human tissue for health, rejuvenation and wellness.

BACKGROUND OF THE INVENTION

It is known that providing laser and LED therapy to targeted human tissue can aid in the repair of damaged tissue. For example, U.S. Pat. Nos. 8,236,037; 8,333,756 and 8,480,720, commonly owned by the applicant, and incorporated into this application in their entirety, describe unique techniques involving scalar technology to provide beneficial therapeutic effect in the treatment of neurological and soft tissue conditions. More specifically, the techniques described in those patents teach the delivery of laser and LED energy to targeted tissue, penetrating the layers of skin to reach internal tissues to produce a specific, non-thermal photochemical effect at the cellular level.

There remains a continual need in the art, however, for even more advancements in the treatment of human tissue for health, rejuvenation and wellness. The present invention provides such improved technology.

BRIEF SUMMARY OF THE INVENTION

The present invention is directed to a system that provides a quantum field of energy that surrounds the body to provide a therapeutic and quantum healing effect to treat human tissue. In one aspect of the invention, the system provides a quantum field of energy around a given area for health, rejuvenation, wellness, electromagnetic frequency protection, balancing or neutralizing of electronic pollution, among other benefits. In another aspect of the invention, the system induces a relaxing environment with the use of scalar wave technology.

In one embodiment, a quantum field system includes a quantum field generating device for treatment of human tissue. The quantum field generating device may include a housing, a printed circuit board contained within the housing, and a plurality of antennas positioned in the housing. The antennas may be electrically connected to the printed circuit board. The printed circuit board includes a microprocessor for controlling signals generated by the antennas. In one aspect, the printed circuit board digitally controls the antennas to provide signal waves having wave differences that are approximately 180 degrees different in phase relative to each other to provide therapeutic effect. In another aspect, the quantum field generating device may provide frequencies between 1 and 100,000 Hz which may be pulsed through the quantum field generating device to provide therapeutic effect. In other aspects, the quantum field system may include control knobs mounted to the housing which are used to change and/or fine tune the programs and thus the operation of the quantum field device.

In an exemplary aspect, the plurality of antennas may be four antennas spaced around the printed circuit board within the housing. Each antenna may be angled approximately forty-five degrees relative to the printed circuit board to emit the signal waves. The phase and/or amplitude relationships between signals emitted by adjacent antennas may be the same or may be different.

In another exemplary aspect, a plurality of input ports may be mounted to the housing. The input ports may include a power input, a USB input, an audio input, and a co-axial cable input.

In yet another aspect, the quantum field device may be mounted to a wall or other structure, or the device may be portable.

Other features and advantages of the invention will become apparent to those skilled in the art upon review of the following detailed description, claims and drawings in which like numerals are used to designate like features.

Figure 1:
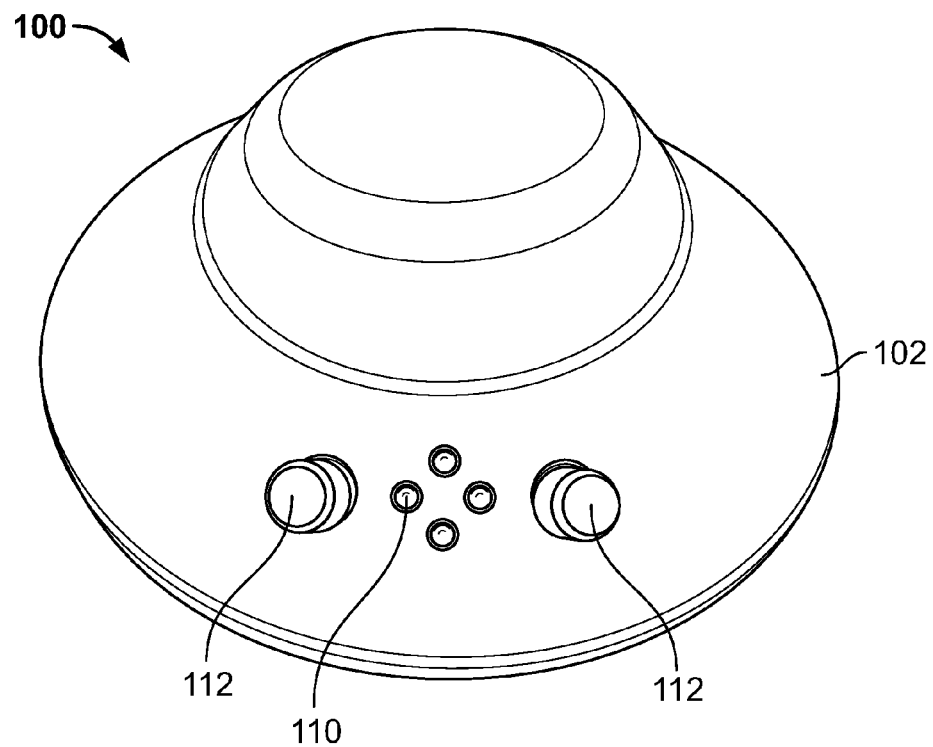
FIG. 1 depicts an isometric top view of an exemplary embodiment of a quantum field generating system of the present invention.
Figure 2:
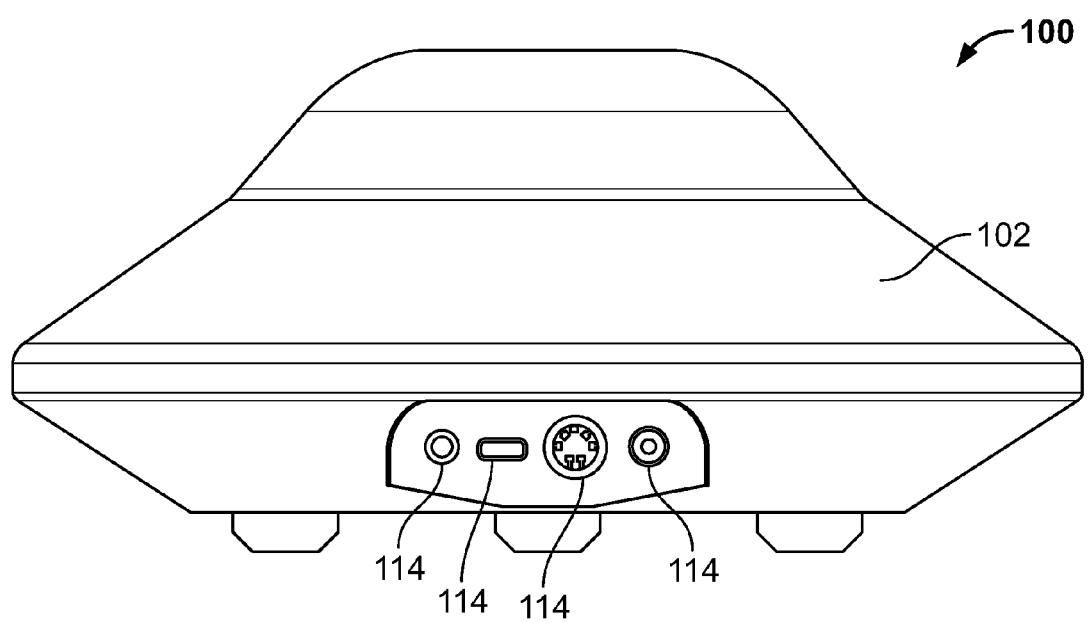
FIG. 2 depicts a side view of the system of FIG. 1.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE EMBODIMENTS

Referring to FIGS. 1-4, in one exemplary embodiment, there is shown a quantum field device 100 that provides a quantum field of energy that surrounds the body to provide a therapeutic and quantum effect to treat human tissue for health, rejuvenation and wellness. The quantum field device 100 may define a housing 102 for containing the components used with the device 100. The housing 102 is designed to not only protect the internal components, it also provides aesthetics to the device 100, and helps with providing the quantum field energetic effect. The housing may define the depicted saucer shape or other possible shapes. The housing may be a two-piece construction or may be a single unitary housing.

The housing may contain a printed circuit board 104 that may be used to digitally program and control a combination of antennas 108 and/or crystal oscillators. The device 100 may provide a quantum field of energy through the use of a microprocessor on the printed circuit board 104 that digitally programs specific frequencies of signals, e.g., sine or scalar wave signals, which are pulsed in a phase relationship with the use of the antennas 108 or with the use of crystal oscillators (or other electronic oscillator circuits that will provide an electrical signal with a precise frequency). In one embodiment, the antennas 108 provide quantum field energy and a scalar effect that is transmitted from the device 100. In one aspect, one or more circuits may be used to provide a desired phase relationship between the signals emitted from the antennas, such as a 180 degree phase relationship. The device 100 may digitally pulse signals within a range of frequencies between 0 and 100,000 hertz and having a 180 degree phase relationship.

Located on the housing 102 may be one or more control knobs 112 for changing and/or fine tuning the programs and thus the operation of the quantum field device 100. For example, one control knob 112 may be used to adjust the internal antenna waveform amplitude. This knob allows the user to adjust or fine tune the settings on the device. The other control knob 112 may be used to allow the user to select one of the multiple preset waveform options. It should be understood that additional controls may be used with the device to further adjust and fine tune the settings of the quantum field device 100.

Also located on the housing near the control knobs 112 are indicator lights 110 that indicate whether the quantum field device is on or off. One or more of these indicators may be spaced apart in a variety of configurations including the illustrated diamond configuration.

Additionally, on the housing may be located multiple input ports 114 which may be used to provide power, additional controls, allow for the uploading of software or other programming, and provide extra features to the quantum field device 100. For example, the quantum field device may include ports 114 for a power input, a USB, a mini USB, an audio input, a co-axial cable input, and a connection with other devices, such as with the laser therapy devices disclosed and depicted in U.S. Pat. No. 8,236,037, the disclosure of which is incorporated herein by reference. Some or all of these ports may be used to help balance and neutralize electromagnetic frequencies (EMF) or electronic pollution, and may be used for inducing a therapeutic effect. It should be understood that other inputs may be used to provide power, additional controls, allow for the uploading of software or other programming, and provide extra features to the quantum field device 100.

The printed circuit board 104 holds and coordinates the various functions and components of the quantum field device 100. For example, the printed circuit board 104 coordinates the function of a microprocessor, crystal oscillators, and the antennas. The printed circuit board also handles the interface between the control knobs 112, indicator lights 110, and the various input ports 114.

As indicated above, the printed circuit board 104 may digitally program specific frequencies of signals, e.g., sine or scalar wave signals, which are pulsed through control circuitry and in a phase relationship with the use of the antennas 108. In one embodiment, the printed circuit board and its microprocessor will control via control circuitry the sending of sine or scalar wave signals that are pulsed to the antennas or crystal oscillators in a 180 degree phase relationship. The printed circuit board and its microprocessor can also control the frequency and amplitude of the signals. These emitted signals from the antennas and their phase relationship provide an energy field and a scalar effect that provide a therapeutic and quantum therapy to treat human tissue for health, rejuvenation and wellness.

In an alternative aspect, the microprocessor may control the phase relationship of the signals to provide signals having a phase relationship that may be greater than or less than 180 degrees. The microprocessor may also control the amplitudes and frequencies of the signals which may be in phase or out of phase. The quantum field device 100 therefore can be programmed and adjusted to any number of signal phase relationships, amplitudes and frequencies to provide the desired therapeutic effect.

In an alternative aspect, the quantum field device 100 may have a plurality of LED's or laser diodes positioned on the housing 102 for emitting therapeutic light having a desired frequency. The LED's or laser diodes may be a waveform controlled light output of scalar wave signals. The device may also include one or more circuits which control the LED's and laser diodes and which may be pulsed in a phase relationship, for example at a 180 degree phase relationship. In another aspect, the LED's or laser diodes may be pulsed at the same or different frequencies. Examples of LED and laser diode configurations which can be used with the device 100 can be found in U.S. Pat. No. 8,480,720, which is incorporated herein by reference.

In another exemplary embodiment, the quantum field device 100 may be fixed to a wall or other structure in a room or may be a portable device that may be easily moved to a different location or carried by a user. The device 100 may be scalable in that it may be configured in different sizes, may include scalable technology, and may be used in a variety of different size rooms, from smaller rooms to a large area or an entire house or building.

Figure 3:
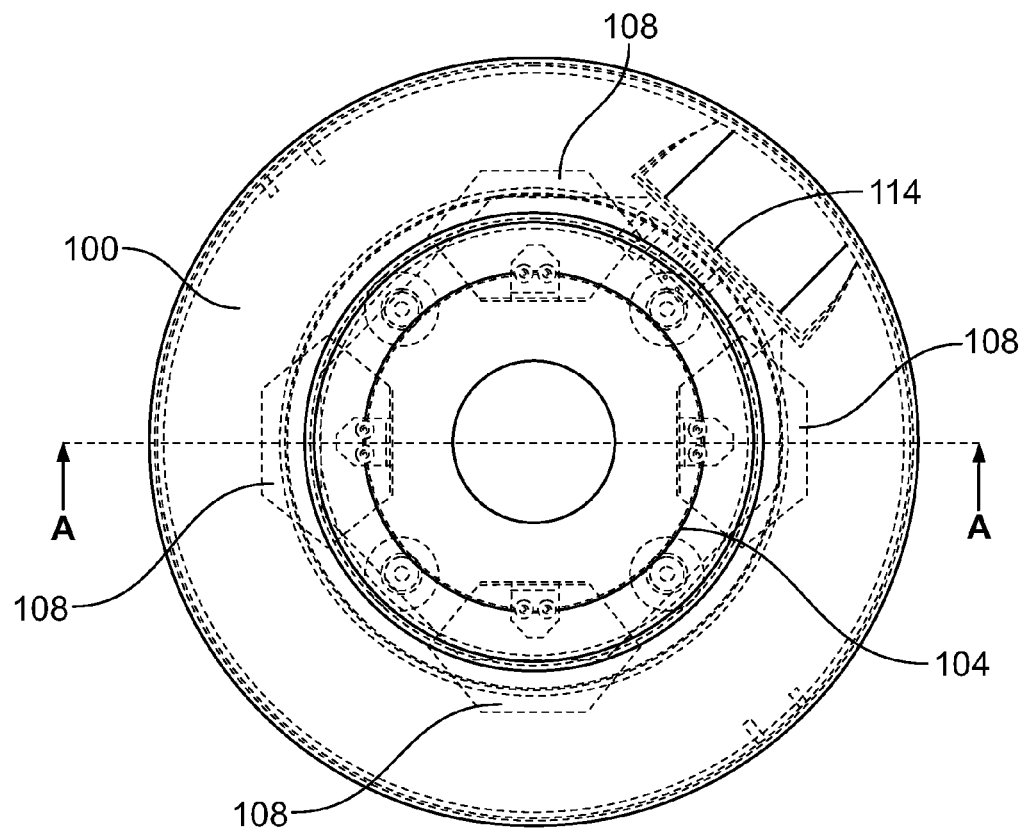
FIG. 3 depicts a top cut-away view of the system of FIG. 1.
Figure 4:
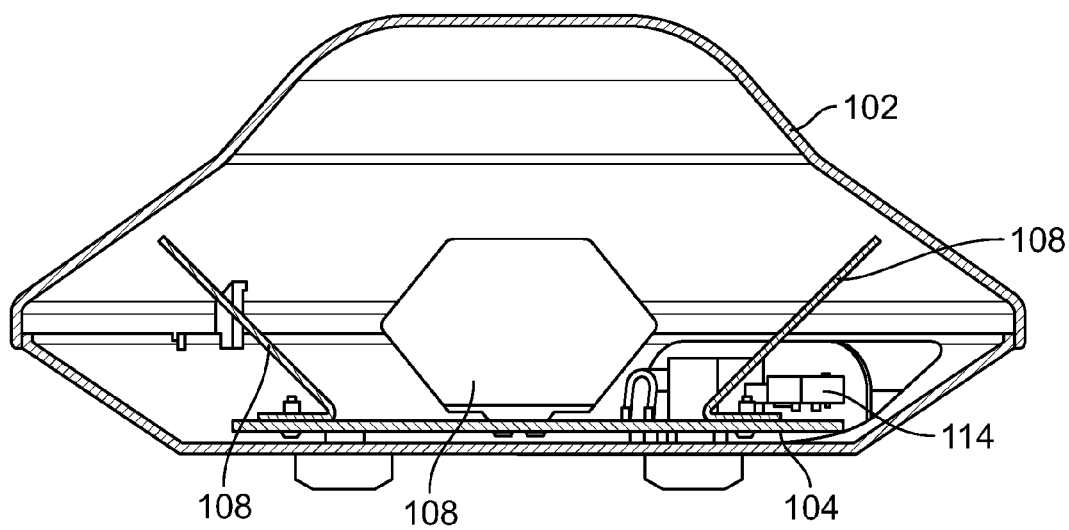
FIG. 4 depicts a side section view of the system of FIG. 3.

The antennas and/or oscillators 108 may be arranged in the exemplary manner depicted in FIG. 3. In one exemplary aspect, four antennas may be spaced equidistant and in a circular manner around the printed circuit board, as shown in FIG. 3. The antennas may be mounted angularly approximately 45 degrees relative to the printed circuit board, as shown in FIG. 4. The panel surface of each angled antenna faces toward the center of the device 100. The antenna panel itself may define the depicted hexagonal shape or may define other shapes.

The antennas may be mounted to the housing through the use of fasteners and the like. It should be understood that other antenna arrays having different spacing and mounting angles may be used with the device 100.

In one embodiment, the adjacent antennas may be programmed to be 180 degrees out of phase with each other, as state above. In this configuration, the antennas will provide phased signals that will provide therapeutic and quantum healing effect.

In another aspect, the device 100 and the microprocessor on the printed circuit board 104 may include the ability to use and modulate nearly any frequency, amplitude and/or phase of signals depending on the desired application and the type of desired quantum field or therapeutic effect.

Variations and modifications of the foregoing are within the scope of the present invention. It should be understood that the invention disclosed and defined herein extends to all alternative combinations of two or more of the individual features mentioned or evident from the text and/or drawings. All of these different combinations constitute various alternative aspects of the present invention.

What is claimed is:

1. A device for treatment of human tissue comprising:
   a housing,
   a printed circuit board contained within the housing, the printed circuit board includes a microprocessor, and
   a plurality of antennas positioned within the housing and electrically connected to the printed circuit board, the plurality of antennas spaced in a circular manner around the printed circuit board, each of the plurality of antennas defines a flat antenna panel surface that extends angularly and above the printed circuit board, each of the plurality of flat antenna panel surfaces are oriented to face toward the center of the housing, the microprocessor of the printed circuit board digitally controlling the signal waves emitted from the antennas to provide signal waves from adjacent antennas having wave differences that are approximately 180 degrees different in phase relative to each other, wherein frequencies between 1 and 100,000 Hz are pulsed through the plurality of antennas.

2. The device of claim 1, further including control knobs mounted to the housing.

3. The device of claim 1, wherein the plurality of antennas are four antennas spaced equidistantly around the printed circuit board within the housing.

4. The device of claim 3, wherein each antenna is angled approximately forty-five degrees relative to the printed circuit board to emit the signal waves.

5. The device of claim 1, further including a plurality of input ports mounted to the housing and operatively connected to the printed circuit board, wherein the input ports are selected from the group consisting of a power input, a USB input, an audio input, and a co-axial cable input.

6. The device of claim 1, wherein the phase or amplitude relationships between adjacent antennas is different.

7. The device of claim 1, further comprising indicator lights on the housing.

8. The device of claim 1, wherein the device is portable.

9. The device of claim 1, wherein the microprocessor controls preset waveforms to be transmitted by the antennas.

10. The device of claim 9, wherein the plurality of antennas include crystal oscillators.

11. The device of claim 10, wherein the printed circuit board coordinates the function of a microprocessor, the crystal oscillators, and antennas.

12. The device of claim 1, further comprising control knobs, indicator lights, and input ports, wherein the printed circuit board coordinates the interface between the control knobs, indicator lights and input ports.

13. The device of claim 1, wherein the microprocessor includes control circuitry that controls the sending of sine or scalar wave signals that are pulsed through the antennas in a 180 degree phase relationship.

14. The device of claim 13, wherein the microprocessor controls the frequency and amplitude of the signal waves.

15. The device of claim 1, further comprising a plurality of light emitting diodes or laser diodes positioned on the housing for emitting light having frequencies that provide therapeutic effect.

16. The device of claim 15, wherein the emitted light is scalar wave signals.

17. The device of claim 16, wherein the scalar wave signals are pulsed in a phase relationship.

* * * * *